United States Patent [19]

Miyazawa et al.

[11] Patent Number: 5,047,561
[45] Date of Patent: Sep. 10, 1991

[54] PROCESS FOR PRODUCING A LACTONE

[75] Inventors: Chihiro Miyazawa; Kazunari Takahashi; Hiroshi Kameo; Shinji Isogai, all of Kurashiki; Masayuki Otake, Yokohama, all of Japan

[73] Assignee: Mitsubishi Kasei Corporation, Tokyo, Japan

[21] Appl. No.: 582,158

[22] Filed: Sep. 14, 1990

[30] Foreign Application Priority Data

| Sep. 27, 1989 [JP] | Japan | 1-249346 |
| Oct. 4, 1989 [JP] | Japan | 1-257960 |
| Oct. 24, 1989 [JP] | Japan | 1-274999 |
| Aug. 3, 1990 [JP] | Japan | 2-206400 |

[51] Int. Cl.$^5$ .................................. C07D 307/33
[52] U.S. Cl. ............................ 549/325; 549/326; 502/213
[58] Field of Search ............... 549/325, 326; 502/213

[56] References Cited

U.S. PATENT DOCUMENTS

| 4,485,245 | 11/1984 | Hsu et al. | 549/325 |
| 4,485,246 | 11/1984 | Lyons | 549/325 |
| 4,620,016 | 10/1986 | Drake et al. | 549/325 |
| 4,892,955 | 1/1990 | Wada et al. | 549/325 |

FOREIGN PATENT DOCUMENTS 2194232 3/1988 United Kingdom .
2203432 10/1988 United Kingdom .

Primary Examiner—C. Warren Ivy
Assistant Examiner—Ba K. Trinh
Attorney, Agent, or Firm—Oblon, Spivak, McClelland, Maier & Neustadt

[57] ABSTRACT

A process for producing a lactone by reacting in a hydrogenation reaction zone a dicarboxylic acid, a dicarboxylic acid anhydride and/or a dicarboxylic acid ester with hydrogen in a liquid phase using a solvent in the presence of a catalyst comprising ruthenium and an organic phosphine, which process comprises the following steps (1) to (6):

(1) a first step of recovering the liquid phase from the hydrogenation reaction zone,
(2) a second step of distilling the liquid phase in a first distillation column to obtain a first distillate and a first residue,
(3) a third step of recycling the first residue to the hydrogenation reaction zone,
(4) a fourth step of distilling a part of the first residue in a second distillation column to obtain a second distillate and a second residue,
(5) a fifth step of recycling the second distillate to the hydrogenation reaction zone or the first distillation column, and
(6) a sixth step of recovering a lactone from the first distillate.

9 Claims, 1 Drawing Sheet

FIGURE 1

PROCESS FOR PRODUCING A LACTONE

The present invention relates to a process for producing a lactone. More particularly, it relates to a process for producing a lactone on an industrial scale by hydrogenating a dicarboxylic acid, a dicarboxylic acid anhydride and/or a dicarboxylic acid ester in a liquid phase.

A method for producing a lactone by hydrogenating a dicarboxylic acid, a dicarboxylic acid anhydride and/or a dicarboxylic acid ester, has been studied since long ago, and various proposals have been made. For example, it is known to conduct the hydrogenation reaction in a fixed bed system or in a suspension liquid phase system using a solid catalyst such as a nickel-type catalyst (Japanese Examined Patent Publication No. 6947/1968), a cobalt-type catalyst (Japanese Unexamined Patent Publication No. 95057/1986), a copper-chromium-type catalyst (Japanese Examined Patent Publication No. 20119/1963) or a copper zinc-type catalyst (Japanese Examined Patent Publication No. 14463/1967).

On the other hand, it is also known to conduct the above hydrogenation reaction by means of a ruthenium catalyst for a homogeneous system. For example, U.S. Pat. No. 3,957,827 discloses a method for producing a lactone by conducting hydrogenation under a pressure of from 40 to 4,000 psi using a ruthenium catalyst of $[RuX_n(PR_1R_2R_3)_xL_y]$ type. Further, it is disclosed in U.S. Pat. No. 4,485,245 that a hydrogenation reaction by means of a similar catalyst is conducted in the presence of an organic amine.

However, in such conventional methods wherein a solid catalyst such as a nickel-type catalyst, a cobalt-type catalyst, a copper-chromium-type catalyst or a copper-zinc type catalyst, is used, it is unavoidable to employ severe reaction conditions such as a temperature of at least 250° C. and a pressure of at least a few tens atm, and there is a problem that decomposition products are substantial, and no adequate yield can be attained. On the other hand, the method of using a ruthenium catalyst for a homogeneous system has a feature that the hydrogenation reaction proceeds under a relatively mild condition, but it also has problems such that the catalytic activity is rather low, the catalytic life is short, and the reaction apparatus is likely to be corroded, since halogen is used.

Under these circumstances, the present applicant has previously proposed a method for conducting hydrogenation in a liquid phase in the presence of a ruthenium catalyst comprising ruthenium, an organic phosphine and a conjugate base of an acid having a pKa of less than 2 using a solvent (Japanese Unexamined Patent Publication No. 25771/1989, U.S. Pat. No. 4,892,955). In this method, a highly active ruthenium catalyst is employed, whereby a lactone can be prepared under a mild condition in good yield.

However, there has been a problem that if the hydrogenation reaction is continued by the ruthenium catalyst using a dicarboxylic acid, a dicarboxylic acid anhydride and/or a dicarboxylic ester as the starting material, high boiling point byproduct tend to accumulate due to the decomposition or polycondensation of the starting material, or the catalyst tends to be deactivated.

Further, in a continuous reaction system, in order to continue the hydrogenation reaction under a stabilized condition for a long period of time while preventing accumulation of high boiling point byproducts, it is common to employ a method wherein a part or whole of the catalyst solution after the reaction is withdrawn out of the system for replacement with a fresh catalyst solution depending upon the production rate of the high boiling point byproducts or the amount of deactivated catalyst. However, the withdrawn catalyst solution contains useful components such as the solvent and the lactone, and effective use of these components has been an important subject yet to be solved for the industrial operation.

The present inventors have conducted an extensive research for a continuous reaction using such a ruthenium catalyst and as a result, have found (1) that in the residue after separation of the desired lactone by distillation, the catalyst still remains in an active state, and such a catalyst may be recycled as it is for use in the next reaction, (2) that in the residue, high boiling point byproducts are contained more or less and will be accumulated to a high concentration when the operation is continued for a long period of time, whereby the catalytic activities will be adversely affected, and (3) that the high boiling point byproducts can be thermally decomposed under a certain condition to produce and recover a lactone. It is an object of the present invention to reduce a lactone economically and industrially advantageously by efficiently utilizing the solvent and the catalyst.

The present inventors have conducted an extensive research with such an object and as a result, have accomplished the following invention for an industrial process for producing a lactone.

Namely, the present invention provides a process for producing a lactone by reacting in a hydrogenation reaction zone a dicarboxylic acid, a dicarboxylic acid anhydride and/or a dicarboxylic acid ester with hydrogen in a liquid phase using a solvent in the presence of a catalyst comprising ruthenium and an organic phosphine, which process comprises the following steps (1) to (6)

(1) a first step of recovering the liquid phase from the hydrogenation reaction zone, (2) a second step of distilling the liquid phase in a first distillation column to obtain a first distillate and a first residue, (3) a third step of recycling the first residue to the hydrogenation reaction zone, (4) a fourth step of distilling a part of the first residue in a second distillation column to obtain a second distillate and a second residue, (5) a fifth step of recycling the second distillate to the hydrogenation reaction zone or the first distillation column, and (6) a sixth step of recovering a lactone from the first distillate.

Now, the present invention will be described in detail with reference to the preferred embodiments.

In the accompanying drawing.

1) Starting material for the reaction

As the starting material for the production of a lactone in the present invention, a saturated or unsaturated dicarboxylic acid having from 3 to 7 carbon atoms, an anhydride thereof or an ester thereof may be mentioned. As the ester, a lower alkyl ester is preferred. Specifically, for example, fumaric acid, succinic acid, maleic anhydride, succinic anhydride, diethyl maleate, diethyl fumarate or di-n-butyl succinate may be employed.

2) Catalyst component

As the catalyst in the present invention, a ruthenium catalyst of $[RuX_n(PR_1R_2R_3)_xL_y]$ type disclosed in the above mentioned U.S. Pat. No. 3,957,827 may be used. However, it is preferred to employ a ruthenium catalyst comprising (1) ruthenium, (2) an organic phosphine and (3) a conjugate base of an acid having a pKa of less than 2 disclosed in U.S. Pat. No. 4,892,955 by the present applicant, as will be described hereinafter.

(1) Ruthenium

The ruthenium may be used in the form of metal ruthenium or a ruthenium compound. As the ruthenium compound, an oxide, halide, hydroxide, inorganic acid salt, organic acid salt or complex compound of ruthenium may be used. Specifically, there may be mentioned ruthenium chloride, ruthenium bromide, ruthenium iodide, ruthenium nitrate, ruthenium acetate, ruthenium acetylacetonate (trisacetylacetoneruthenium), sodium hexachlororuthenate, dipotassium-tetracarbonylruthenate, pentacarbonylruthenium, cyclopentadienyldicarbonylruthenium, dibromotricarbonylruthenium, chlorotris(triphenylphosphine)hydridoruthenium, bis(tri-n-butylphosphine)tricarbonylruthenium, dodecacarbonyltriruthenium, tetrahydridodecacarbonyltetraruthenium, dicesium octadecacarbonylhexaruthenate and tetraphenylphosphonium undecacarbonylhydridetriruthenate.

Such metal ruthenium or ruthenium compound is used usually in an amount such that the concentration in the reaction solution will be 0.01 to 100 mmol, preferably from 0.1 to 10 mmol, as ruthenium, in one liter of the reaction solution.

(2) Organic phosphine

The organic phosphine is an essential component which contributes to the control of the electron state of ruthenium of (1) as the main catalyst and to the stabilization of the activity of ruthenium. Specific examples of such an organic phosphine include a trialkylphosphine such as trioctylphosphine, tri-n-butylphosphine or dimethyl-n-octylphosphine, a tricycloalkylphosphine such a tricyclohexylphosphine, a triarylphosphine such as triphenylphosphine, an alkylarylphosphine such as dimethylphenylphosphine, and a polyfunctional phosphine such as 1,2-bis(diphenylphosphino)ethane.

Such an organic phosphine is used usually in an amount within a range of from 1 to 100 mol, preferably from 3 to 20 mol, per mol of ruthenium.

(3) Conjugate base of an acid having a pKa of less than 2

The conjugate base of an acid having a pKa of less than 2 is not an essential component to the ruthenium catalyst. However, it is useful as an additional accelerator for the catalyst and also has a function to maintain the organic phosphine stable in the reaction system. It may be any material so long as it is capable of forming a conjugate base of an acid having a pKa of less than 2 during the preparation of the catalyst or in the reaction system. It may be supplied in the form of a Bronsted acid having a pKa of less than 2, or a salt of such an acid. Specifically, there may be mentioned inorganic acids such as sulfuric acid, sulfurous acid, nitric acid, nitrous acid, perchloric acid, phosphoric acid, borofluoric acid, hexafluorophosphoric acid, tangustic acid, phosphomolybdic acid, phosphotangstic acid, silicontangstic acid, polysilicic acid and fluorosulfonic acid, and organic acids such as trichloroacetic acid, dichloroacetic acid, trifluoroacetic acid, methanesulfonic acid, trifluoromethanesulfonic acid, lauryl sulfonic acid, benzensulfonic acid and p-toluenesulfonic acid, or ammonium salts or phosphonium salts of these acids.

It may be added in the form of an acid derivative which is capable of forming such a conjugate base in reaction system. For example, it may be added in the form of an acid halide, an acid anhydride, an ester or an acid amide to the reaction system to obtain similar effects.

Such an acid or base is used usually in an amount within a range of from 0.5 to 100 mol, preferably from 1 to 20 mol, per mol of ruthenium.

3) Solvent for reaction

For the hydrogenation reaction. the starting material or the reaction product may itself be used as a solvent. In addition, the following various solvents may be employed.

Such solvents include ethers such as diethyl ether, anisole, tetrahydrofuran, ethylene glycol diethyl ether, triethylene glycol dimethyl ether and dioxane; ketones such as acetone, methyl ethyl ketone and acetophenone; alcohols such as methanol, ethanol, n-butanol, benzylalcohol, ethylene glycol and diethylene glycol; phenols; carboxylic acids such as formic acid, acetic acid, propionic acid and toluic acid; esters such as methyl acetate, n-butyl acetate and benzyl benzoate; aromatic hydrocarbons such as benzene, toluene, ethylbenzene and tetralin; aliphatic hydrocarbons such n-hexane, n-octane and cyclohexane; halogenated hydrocarbons such as dichloromethane, trichloroethane and chlorobenzene; nitrohydrocarbons such as nitromethane and nitrobenzene; carboxylic acid amides such as N,N-dimethylformamide, N,N-dimethylacetoamide and N-methylpyrrolidone; other amides such as hexamethylphospholic acid triamide and N,N,N',N'-tetraethylsulfamide; ureas such as N,N'-dimethylimidazolidone and N,N,N',N'-tetramethylurea; sulfones such as dimethylsulfone and tetramethylene sulfone; sulfoxides such as dimethylsulfoxide and diphenylsulfoxide; lactones such as γ-butyrolactone and α-caprolactone; polyethers such as triglyme (triethylene glycol dimethyl ether), tetraglyme (tetraethylene glycol dimethyl ether) and 18-crawn-6; nitriles such as acetonitrile and benzonitrile and carbonates such as dimethyl carbonate and ethylene carbonate.

As described above, various solvents may be used for the hydrogenate reaction. However, for the continuous process of the present invention, the solvent is required to be a solvent having a boiling point higher than the lactone as the desired product. In this respect, polyethers may, for example, be suitably employed.

4) Preparation and supply of a catalyst solution

The ruthenium catalyst may, for example, be prepared by heat-treating in an inert gas atmosphere a solution containing the above described respective catalyst components. The synthesized catalyst is considered to have a complex structure wherein from 2 to 4 organic phosphines are coordinated per one ruthenium atom. Only an excess organic phosphine not constituting the complex is quantitatively analyzed as free organic phosphine by gaschromatography.

In a case where a conjugate salt of an acid having a pKa of less than 2 is present in the catalyst system, the concentration of the free organic phosphine further decreases. Therefore, it is believed that a stable complex is formed also between the conjugated base and the organic phosphine in the solution.

The concentration of the free organic phosphine in the liquid phase in the hydrogenation reaction zone is preferably maintained usually within a range of from 0.01 to 0.1% by weight, more preferably from 0.02 to 0.05% by weight. If the concentration is outside such a range, the yield of the lactone tends to be low. In a case where the free organic phosphine has a high concentration exceeding 0.1% by weight, it is likely to react with the starting material to form high boiling point by-product, and the influence of such a side reaction is believed to be attributable to the decrease in yield. On the other hand, if the free organic phosphine is at a low concentration of less than 0.01% by weight, even the organic phosphine in the ruthenium complex is likely to be consumed by such a side reaction. In such a case, precipitation of ruthenium metal is observed in the reaction solution, and the deterioration of the catalytic activity tends to be remarkable.

Further, the organic phosphine is very oxidizable, and it is known that the organic phosphine is consumed as an organic phosphine oxide during the continuous operation. Therefore, it is necessary to consider supplementation to complement the consumption.

There is no particular restriction as to a method for maintaining the concentration of the free organic phosphine in the hydrogenation reaction zone within the above mentioned range. However, it is possible to employ, for example, a method of supplying a fresh catalyst solution to the hydrogenation reaction zone, or a method of supplementing only an organic phosphine solution separately.

5) Hydrogenation reaction

To conduct the hydrogenation reaction by the process of the present invention, the above mentioned starting material, the catalyst component and the solvent are introduced into a reactor, and hydrogen is continuously introduced thereto. Hydrogen may be the one diluted with a gas inert to the reaction, such as nitrogen, methane or carbon dioxide, and the gas hourly space velocity (GHSV) is usually at least 2 $hr^{-1}$, preferably at least 10 $hr^{-1}$ The reaction temperature is usually from 50 to 250° C., preferably from 100 to 220° C. The hydrogen partial pressure in the reaction system is not particularly limited, but is usually from 0.1 to 100 $kg/cm^2G$, preferably from 1 to 100 $kg/cm^2G$, more preferably from 10 to 50 $kg/cm^2G$, from the practical point of view. The reaction is preferably conducted in a continuous system. However, the reaction may be conducted in a batch system so that the flow will be intermittent.

The concentration of water in the liquid phase in the hydrogenation reaction zone is controlled usually at a level of not higher than 1% by weight, preferably not higher than 0.5% by weight, more preferably not higher than 0.3% by weight. If the water content in the reaction solution is maintained within the above range, the conversion of the starting material increases, and the selectivity and the yield of the desired product will be improved.

As a method for reducing the concentration of water, it is possible to employ, for example, a method wherein among the above reaction conditions, the hydrogen flow rate is increased so that the water content is removed out of the hydrogenation reaction zone, or a method wherein the reaction temperature is raised to increase the distribution of water to the gas phase and thereby to reduce the water content in the liquid phase.

6) Process steps after the hydrogenation reaction zone

Figure 1:
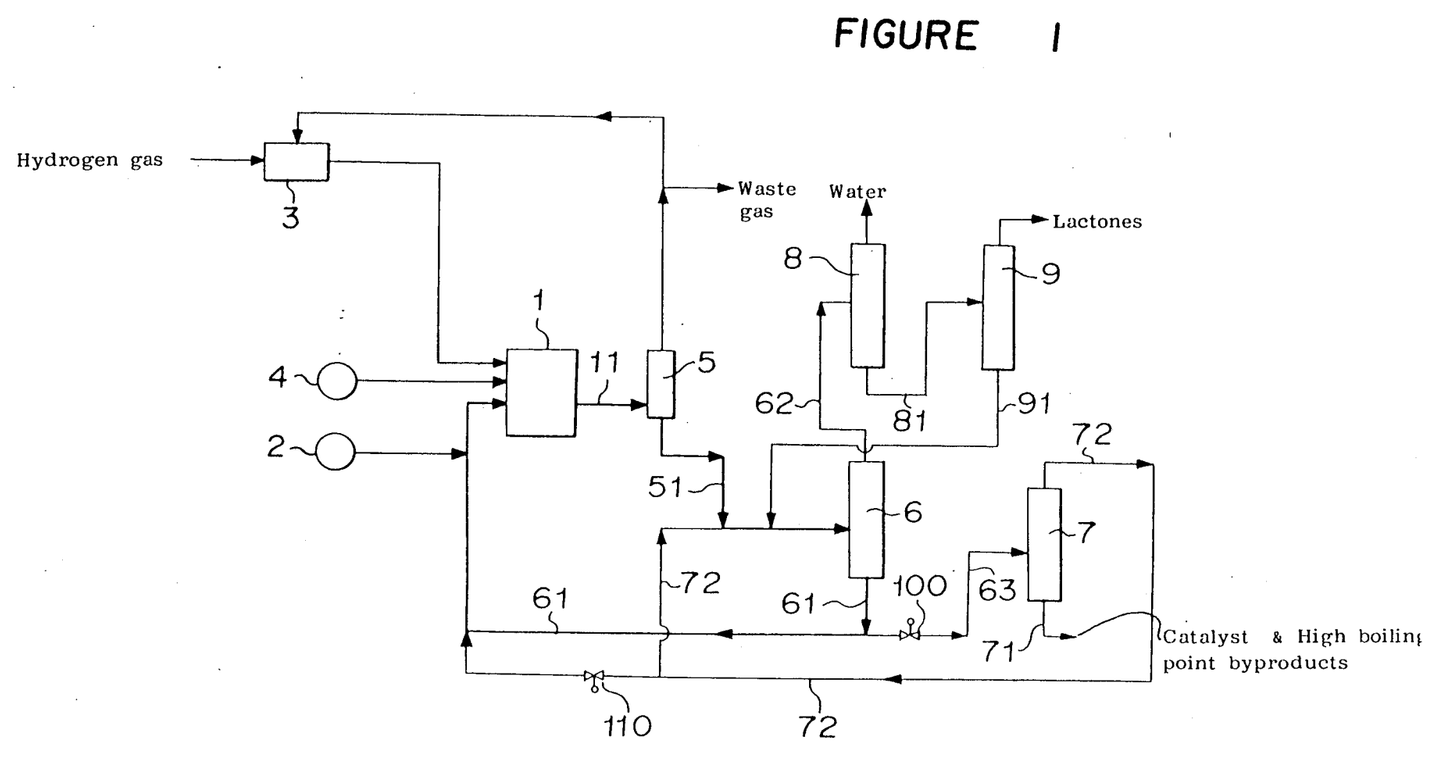
FIG. 1 is a flow chart of a continuous reaction system used for carrying out the process of the present invention.

The process steps after the hydrogenation reaction zone will be described with reference to FIG. 1. FIG. 1 is a flow chart of one embodiment of a continuous reaction system which may be employed for carrying out the process of the present invention. In FIG. 1, reference numeral 1 indicates a reactor, numeral 2 indicates a container for the catalyst solution, numeral 3 indicates a compressor, numeral 4 indicates a container for the starting material, numeral 5 indicates a gas-liquid separator, numeral 6 indicates a first distillation column, numeral 7 indicates a second distillation column, numeral 8 indicates a third distillation column, and numeral 9 indicates a fourth distillation column.

(1) First step

The liquid phase is recovered from the hydrogenation reaction zone.

Namely, the reaction mixture discharged through a conduit 11 from the reactor 1 (the hydrogenation reaction zone) is cooled and then separated into a gas phase and a liquid phase by the gas-liquid separator 5. Here, it is also possible to employ a method wherein only a liquid phase portion of the reaction mixture is withdrawn from the reactor 1, and only the gas phase portion is introduced to the gas-liquid separator 5 and cooled, and the lactone vapor accompanying in the gas phase is recovered as a liquid phase under atmospheric pressure.

The gas phase composed mainly of hydrogen can be recycled to the hydrogenation reaction zone. Further, it is possible to employ a method wherein a part of the gas phase is purged, or a method wherein methane-forming reactor (methanater) is provided in a circulatory route of the gas phase, whereby carbon monoxide formed in the gas phase will be converted to methane and thus detoxified.

(2) Second step

The liquid phase is distilled in a first distillation column 6 to obtain a first distillate and a first residue.

Namely, the liquid phase recovered in the first step is supplied through a conduit 51 to the first distillation column 6, whereby distillation is conducted. In a case where lactones are separated from the solvent, catalyst, etc. by distilling the liquid phase containing the lactones, solvent, catalyst, unreacted starting material and water, it is usually required to employ a distillation column of 40 plates or more and to have a large reflux ratio. In a distillation column having a high plate number, the pressure difference in the column is substantial, and the bottom pressure rises to bring about a very high temperature, thus leading to a deterioration of the catalytic activities or decomposition of the solvent. Further, if the reflux ratio is made large, the energy loss will be substantial, such being uneconomical.

Accordingly, it is preferred to use a column having a relatively small number of plates as the first distillation column, and the reflux ratio is set at a relatively small level, whereby from the top of the column, a liquid containing 3 to 50% by weight of the solvent together with lactones and water, is distilled as a first distillate from a conduit 62. Further, it is possible to adopt a system wherein a plurality of distillation columns are operated in parallel so that the entire system functions as the first distillation tower.

On the other hand, from the bottom of the first distillation column, a liquid containing an unreacted material, an excess solvent and the catalyst, is withdrawn as the first residue though a conduit 61.

(3) Third step

The first residue is recycled to the hydrogenation reaction zone.

Namely, the first residue containing the catalyst and the solvent is returned via the conduit 61 to the reactor 1.

(4) Fourth step

A part of the first residue is distilled in a second distillation column 7 to obtain a second distillate and a residue.

If in the third step, all the first residue is recycled to the hydrogenation reaction zone and the continuous operation is conducted, high boiling byproducts tend to accumulate due to the decomposition or polycondensation of the starting material, and deactivation of the catalyst is likely to be a problem. Therefore, in the fourth step of the present invention, a part of the first residue is continuously or intermittently withdrawn by operating a valve 100 and subjected to distillation treatment under a certain specific temperature condition in the second distillation column 7, whereby the solvent is recovered as the second distillate from a conduit 72. Further, as an important discovery by the present inventors, it has been found that by this distillation treatment, high boiling by-products in the first residue undergo thermal decomposition to form the desired lactones, which can be recovered. Accordingly, not only the reaction solvent recovered as the second distillate, but also lactones can be recovered by the thermal decomposition of the high boiling point byproducts. Thus, this is significant from the viewpoint of the industrial application. On the other hand, from the bottom of the column, a liquid containing high boiling point byproducts and the catalyst, is withdrawn as the second residue though a conduit 71 at optional timing.

The amount of the first residue to be withdrawn, is usually determined based on the amount of production of the high boiling point byproducts in the catalyst solution or on the amount of deactivated catalyst. However, a larger amount may be withdrawn.

The bottom temperature of the second distillation column 7 is usually from 140 to 240° C., preferably from 160 to 230° C. If the bottom temperature is higher than 240° C., the catalyst tends to be deactivated when the second distillate recovered from the distillation is recycled for use for the hydrogenation reaction. The reason is not clearly understood, but it is conceivable that a catalyst poison is formed by the treatment of the high boiling point byproducts at a very high temperature. Further, when the bottom temperature is lower than 140° C., the high boiling point byproducts in the resulting solution will not be decomposed and tend to accumulate, whereby the yield of lactones and the recovery rate of the solvent tend to be low.

The column top pressure in the solvent distillation is not critical and is usually selected within a range of from 0.01 mmHg to atmospheric pressure, whereby the bottom temperature can be maintained within a range of from 140 to 240° C. Further, the reflux ratio, the number of plates and the residence time at the bottom in the solvent distillation are not critical and may usually be set within such ranges as from 0.01 to 100, from a single plate to 100 plates, and from a few hours to a few tens hours, respectively. As the distillation system, steam distillation, thin film distillation or the like may be employed. Further, it is possible to employ a system wherein a plurality of distillation columns are operated in parallel, so that the entire system functions as the second distillation column.

(5) Fifth step

The second distillate is recycled to the hydrogenation reaction zone 1 or the first distillation column 6.

The second distillate recovered by distillation may directly be returned to the first reactor 1 (hydrogenation reaction zone). However, in the recovered second distillate, not only the solvent but also lactones are contained. Therefore, it is advantageous to return it to the first distillation column for separating lactones from the hydrogenation reaction solution, via a conduit 72 while closing the valve 110 as shown in FIG. 1.

(6) Sixth step

Lactones are recovered from the first distillate.

The first distillate contains lactones as one of the main components and further contains the solvent having a boiling point higher than the lactones as well as water formed by the hydrogenation reaction and other low boiling point reaction byproducts such as organic acids.

Lactones are products for which high quality is required. Accordingly, it is disadvantageous in the case of producing lactones on a commercial scale that impurities are included even in a very small amount. To solve this problem is an important subject for the production of lactones. As a method for recovering lactones, it is common to employ a method wherein the above components are separated by a multi-stage distillation.

For example, in FIG. 1, the first distillate from the first distillation column 6 is supplied via a conduit 62 to the third distillation column 8, whereby distillation is conducted so that low boiling components such as water are distilled from the top of the column. Whereas the bottom solution composed mainly of lactones and the solvent is introduced via a conduit 81 to the fourth distillation column 9, whereby lactones as the final product are obtained from the top of the column. On the other hand, the bottom residue of the fourth distillation column composed mainly of the solvent is also preferably recovered and reused from the industrial viewpoint. Namely, as shown in FIG. 1, it may be recycled via a conduit 91 to the first distillation column 6, or it may be recycled to the reactor 1.

As another method, it is possible to employ a method wherein in the third distillation column, lactones and low boiling point components such as water are distilled, and the solvent is separated as the bottom. The lactone component in the distillate can readily be purified by e.g. distillation.

However, it is known that depending upon the distillation condition, a part of the solvent is decomposed whereby the solvent will be colored, which in turn lowers the quality of the product. Therefore, it is necessary to take this into consideration when the distillation conditions are to be set up.

For example, when a polyether suitable as a solvent for the hydrogenation reaction is used, the bottom temperatures of the third and fourth distillation columns are maintained usually at a temperature of not higher than 150° C., preferably not higher than 130° C. The lower limits for the bottom temperatures are not critical so long as the distillation can be conducted and are usually at least 20° C. The residence time of the bottom residue in the distillation columns is required to be at least 30 minutes from the practical point of view. However, it is not advisable to take a long residence time, as the decomposition rate of the solvent increases. For example, when the bottom temperature is 150° C, the residence time is preferably maintained at a level of not longer than 6 hours, preferably not longer than 3 hours.

To conduct the distillation at a bottom temperature of not higher than 150° C., the degree of the pressure reduction at the top may be adjusted. For example, by adjusting the degree of the pressure reduction at the top to a level of from 30 to 10 mmHg, the bottom temperature can be maintained at a level of from 130 to 150° C. Further, the control of the residence time of the bottom residue in the distillation column can be conducted by adjusting the heat conduction area of the heat exchanger or the temperature difference of the bottom residue and the heating medium of the column.

By the above described process, it is possible to obtain lactones of high quality by controlling the decomposition of the solvent containing in the first distillate to a negligible level and preventing the coloring of the solvent.

Now, the present invention will be described in further detail with reference to Examples. However, it should be understood that the present invention is by no means restricted to such specific Examples.

1. The analytical methods employed are as follows.

(1) The quantitative analyses of the reaction products and the solvent components were conducted by gaschromatography and gel permeation chromatography (GPC).

(2) The concentrations of the free organic phosphine in the catalyst solution and in the reaction solution were obtained by gaschromatography.

(3) The water content in the liquid phase in the reactor was determined by a Karl Fischer water content meter.

(4) With respect to the degree of coloring of the separated product after the distillation was analyzed by the following Monsanto method.

Into a 300 ml flat bottom flask with ground stopper, which was washed and dried, 100 ml of a sample was introduced. While stirring the sample, 8 ml of 98 wt % concentrated sulfuric acid was added at room temperature of not higher than 30° C. at a rate of 2 ml/min by means of a 25 ml burette. The stopper was put on the flask, and the flask was immersed in a water bath of 98±2° C. for 2 hours. Then, after cooling with water to room temperature, 100 ml of the sample was transferred to a flat bottom glass color comparison tube having an inner diameter of 25 mm and a height of 270 mm and visually compared with the same amount of APHA color standard solutions in similar color comparison tubes, whereupon the APHA value with the same color was taken as the measured value.

The composition of the APHA color stock solution was as follows:

| | |
|---|---|
| Potassium chloroplatinate ($K_2PtCl_6$) | 1.245 g |
| Cobalt chloride ($CoCl_2.6H_2O$) | 1.000 g |
| 98% concentrated sulfuric acid | 100 ml |

The above components were put into a 1,000 ml measuring flask and dissolved by an addition of distilled water. Then, the volume was adjusted accurately to 1,000 ml with distilled water. The solution thus obtained was APHA 500, and this solution was diluted with distilled water to obtain standard solutions for lower APHA values.

2. Abbreviations used in the Examples are as follows

TOP: Trioctyl phosphine
GBL: γ-Butyrolactone
HB: High boiling point byproducts
DEGME: Diethylene glycol monomethyl ether 3. "Parts" means "parts by weight"

EXAMPLE 1

(1) Preparation of a catalyst solution 5.6 parts of ruthenium acetylacetonate, 51 parts of TOP and 22 parts of p-toluenesulfonic acid were dissolved in triethylene glycol dimethyl ether (hereinafter referred to simply as "triglyme") and adjusted to a total volume of 10,000 parts. This solution was heat-treated at 200° C. for 2 hours in a nitrogen atmosphere to obtain a catalyst solution (hereinafter referred to as catalyst solution (1)). Here, the concentration of free TOP was 0.04% by weight.

(2) Hydrogenation reaction

Using the continuous reaction system as shown in FIG. 1, the hydrogenation reaction was conducted. Catalyst solution (1) was supplied from the container 2 for catalyst solution to the reactor 1 (200 ml autoclave) at a flow rate of 500 ml/hr, whereby the flow route (conduits: 11→51→61) shown by a broad line in FIG. 1 from the reactor 1 via the gas-liquid separator 5, the first distillation column 6 to the reactor 1, was filled with the catalyst solution. Then, the same solution was circulated to the reactor 1 at the same flow rate. Then, hydrogen gas was supplied to the reactor 1 from the compressor 3 at a flow rate of 800 NTP l/hr to maintain the pressure of the reactor 1 at 40 kg/cm²G and the temperature at 205° C. On the other hand, the starting material solution comprising 80% by weight of succinic anhydride and 20% by weight of GBL was continuously supplied to the reactor 1 from the container 4 for starting material at a flow rate of 100 g/hr to conduct the hydrogenation reaction. Here, the TOP concentration in the liquid phase in the reactor was 0.03% by weight, and the concentration of water was 0.27 % by weight.

(3) Treatment of the reaction solution

The reaction mixture was cooled to 60° C. via the conduit 11 and subjected to gas-liquid separation under atmospheric pressure in the gas-liquid separator 5. A part of the separated gas phase was purged as waste gas, and the major portion of the gas phase was recycled via the compressor 3 to the reactor 1. On the other hand, the liquid phase was supplied to the first distillation column 6 via the conduit 51.

The specification of the first distillation column and the operational conditions were as follows.

| Number of actual plates: | 30 plates |
|---|---|
| Pressure at the top of the column: | 30-10 mmHg |
| Temperature at the bottom of the column: | 130-150° C. |
| Reflux ratio: | 10 |
| Residence time of the bottom residue | 1.5 hours |

By the distillation, a first distillate containing 47% by weight of GBL, 9% by weight of water and 44% by weight of the solvent, was distilled from the top of the column. As will be described hereinafter, GBL as the product was obtained from the first distillate. On the other hand, a first residue containing the catalyst, the solvent and unreacted material, was recycled to the reactor 1 via the conduit 61 at a rate of 100 ml/hr.

The composition of the first residue was as follows.

| Succinic anhydride and succinic acid: | 1.7 wt % |
|---|---|
| GBL: | 3.1 wt % |
| Triglyme | 75.2 wt % |
| HB: | 20.0 wt % |

Then, after one day from the initiation of the reaction, a part of the first residue was withdrawn at a rate of 28 ml/hr via the conduit 63, and this was supplied to the second distillation column 7. At the same time, from the container 2 for catalyst solution, the catalyst solution was supplied to the reactor 1 at a rate of a 28 ml/hr.

The specification of the second distillation column and the operational conditions were as follows.

| Number of actual plates: | 3 plates |
|---|---|
| Pressure at the top of the column: | 200-30 mmHg |
| Temperature at the bottom of the column: | 180° C. |
| Reflux ratio: | 1.0 |
| Residence time of the bottom residue | 1.5 hours |

By the distillation, a second distillate comprising 92.2% by weight of triglyme and 7.8% by weight of GBL was distilled from the top of the column and circulated to the first distillation column 6 via the conduit 72.

The second residue at the bottom containing the catalyst and high boiling components, was purged out of the system through the conduit 71.

Further, with respect to the second distillate, the amount of triglyme, GBL and HB in the first residue were calculated, whereby the following values were obtained.

| Recovery rate of triglyme: | 99.3% |
|---|---|
| Recovery rate of GBL: | 203.8% |
| Decomposition rate of HB: | 16.0% |

(4) Purification of the lactone

The first distillate was supplied to the third distillation column 8 via the conduit 62.

The specification of the third distillation column and the operational conditions were as follows.

| Number of actual plates: | 30 plates |
|---|---|
| Pressure at the top of the column: | 30-10 mmHg |
| Temperature at the bottom of the column: | 90-120° C. |
| Reflux ratio: | 10 |
| Residence time of the bottom residue | 1.5 hours |

By the distillation, water was distilled from the top of the column, and the residue at the bottom comprising by weight of GBL and 67% by weight of the solvent, was supplied to the fourth distillation column 9 via the conduit 81.

The specification of the fourth distillation column and the operational conditions were as follows.

| Number of actual plates: | 35 plates |
|---|---|
| Pressure at the top of the column: | 20 mmHg |
| Temperature at the bottom of the column: | 125° C. |
| Reflux ratio: | 10 |
| Residence time of the bottom residue | 3 hours |

At the fourth distillation column 9, a distillate (GVL) was distilled from the top of the column. The bottom residue composed mainly of the solvent was circulated to the first distillation column 6 via the conduit 91.

The composition of the distillate from the fourth distillation column was as follows.

| GBL: | 99.96 wt % |
|---|---|
| DEGME: | 0.04 wt % |
| Water content: | <0.01 wt % |
| Triglyme: | <0.01 wt % |

No coloring was observed (APHA value: less than 10), and GBL with a very high quality was obtained.

In the above described manner, the operation was conducted continuously for 100 days, whereby after the second day, constant reaction results were obtained. The reaction results after the second day were as follows on the average.

| Conversion of succinic anhydride: | 99.2% |
|---|---|
| Yield of GBL: | 92.2% |
| Formation of HB: | 7.0% |

EXAMPLE 2

The operation was conducted in the same manner as in Example 1 except that the operational conditions of the second distillation column 7 were changed as follows.

Namely, the distillation in the second distillation column was conducted by changing the pressure at the top of the column from 600 to 60 mmHg so that the temperature at the bottom of the column was maintained at 220° C. constantly. The distillate was analyzed, and the results were as follows.

| Composition of the distillate: | |
|---|---|
| triglyme: | 86.7 wt % |
| GBL: | 13.3 wt % |
| Recovery rate of triglyme: | 99.5% |
| Recovery rate of the GBL: | 369.7% |
| Decomposition rate of HB: | 41.8% |

Further, the reaction results (conversion of succinic anhydride, yield of GBL) were the same as in Example 1. Examples 3 to 6 and Reference Example In Example 1, distillation was conducted by variously changing only the conditions for the second distillation column, and the second distillate (recovered solvent) was sampled. 30 ml of the second distillate and 30 ml of a fresh catalyst solution (1) were charged into a SUS autoclave, and 6 g of succinic anhydride was further added thereto. After flushing with nitrogen gas, hydrogen gas was introduced, and the hydrogenation reaction was conducted at 200° C. at 40 kg/cm²G for 2 hours. After the reaction, the reaction solution was analyzed by gas chromategraphy. Further, for the purpose of comparison, the hydrogenation reaction of succinic anhydride was conducted in the same manner as above except that 30 ml of fresh triglyme was used instead of the above distillate, and the analysis was conducted. The results are shown in Table 1.

TABLE 1

|  | Distillation conditions | | Results of analysis of the distillate | | | Reaction results | |
|---|---|---|---|---|---|---|---|
|  | Temp. at the bottom of the column (°C.) | Pressure at the top of the column (mmMg) | A (%) | B (%) | C (%) | Conversion (%) | Yield (%) |
| Example 3 | 180 | 200–30 | 99.3 | 203.8 | 16.0 | 92.5 | 86.0 |
| Example 4 | 220 | 600–60 | 99.5 | 369.7 | 41.8 | 91.8 | 85.2 |
| Example 5 | 255 | 760–100 | 99.9 | 430.3 | 51.2 | 75.9 | 68.3 |
| Example 6 | 128 | 10–0.1 | 87.6 | 120.1 | 3.6 | 91.8 | 85.2 |
| Ref. Example | — | — | Fresh solvent was used | | | 92.0 | 85.7 |

Notes:
A: Recovering rate of triglyme
B: Recovering rate of GBL
C: Decomposition rate of HB From the above results, it is evident that a solution containing the solvent and GBL can be recovered by operating the second distillation column under the respective conditions and that the recovered solution can be reused as a solvent for reaction. Further, it is evident that to satisfy both purposes of recovering GBL and reusing the solvent, the temperature at the bottom of the second distillation column is preferably at a level of from 140 to 240° C.

EXAMPLES 7 and 8

The operation was conducted in the same manner as in Example 1 except that the operational conditions for the fourth distillation column 9 were changed. The operational conditions for the fourth distillation column and the results of the analysis of the residue are shown in Table 2 together with those of Example 1. Further, the composition of the distillate was also analyzed, whereby GBL was found to be at least 99.5% in each case. Slight coloring was observed in the distillate of Example 8.

TABLE 2

|  | Temp. at the bottom of the column (°C.) | Residence time of the bottom residue (hr) | Decomposition rate of the solvent (*) | Coloring of the bottom residue (APHA value) |
|---|---|---|---|---|
| Example 1 | 125 | 3.0 | $1.4 \times 10^{-3}$ | less than 10 |
| Example 7 | 145 | 6.0 | $4.0 \times 10^{-3}$ | less than 20 |
| Example 8 | 175 | 8.0 | $6.0 \times 10^{-2}$ | less than 50 |

(*): The decomposition rate was calculated by the following equation from the amount of DEGME as a decomposition product of the solvent: Decomposition rate = Decomposed product (mol/hr)/supplied solvent (mol/hr)

EXAMPLES 9 to 16

The first distillate from the first distillation column in Example 1 was sampled and subjected to distillation under various conditions, whereby GBL and water were distilled from the top of the column to separate them from the bottom residue composed mainly of the solvent.

The decomposition rate of the solvent supplied to the distillation column was determined from the amount of DEGME as the decomposition product of triglyme contained in the above distillate and the bottom residue, respectively, and the coloring degree of the bottom residue was measured. The results are shown in Table 3.

From the results in Tables 2 and 3, it is evident that the decomposition rate of the solvent is substantially affected by the conditions of the temperature at the bottom of the column and the residence time of the bottom residue.

TABLE 3

|  | Temp. at the bottom of the column (°C.) | Residence time of the bottom residue (hr) | Decomposition rate of the solvent (*) | Coloring of the bottom residue (APHA value) |
|---|---|---|---|---|
| Example 9 | 130 | 3.0 | $1.5 \times 10^{-4}$ | less than 10 |
| Example 10 | 140 | 3.3 | $2.7 \times 10^{-4}$ | 10 |
| Example 11 | 150 | 1.1 | $1.3 \times 10^{-4}$ | less than 10 |
| Example 12 | 150 | 2.4 | $4.1 \times 10^{-4}$ | 10 |
| Example 13 | 150 | 3.4 | $7.8 \times 10^{-4}$ | 10 |
| Example 14 | 150 | 6.0 | $5 \times 10^{-3}$ | 20 |
| Example 15 | 150 | 10.0 | $2 \times 10^{-2}$ | 40 |

TABLE 3-continued

| | Temp. at the bottom of the column (°C.) | Residence time of the bottom residue (hr) | Decomposition rate of the solvent (*) | Coloring of the bottom residue (APHA value) |
|---|---|---|---|---|
| Example 16 | 170 | 10.0 | $2 \times 10^{-2}$ | 40 |

(*): The decomposition rate was calculated by the following equation from the amount of DEGME as a decomposition product of the solvent: Decomposition rate = Decomposed product (mol/hr)/supplied solvent (mol/hr)

EXAMPLES 17 to 19

(1) Preparation of a catalyst solution 3.9 parts of ruthenium acetylacetonate, 37 parts of TOP and 16 parts of p-toluenesulfonic acid were dissolved in triglyme and adjusted to a total volume of 10,000 parts. This solution was heat-treated at 200° C. for 2 hours in a nitrogen atmosphere to obtain a catalyst solution. Here, the concentration of free TOP was 0.043% by weight.

(2) Hydrogenation reaction and treatment of the reaction solution

Using the above catalyst solution, the continuous operation was conducted for 30 days under the same conditions as in Example 1. However, in these Examples, referring to FIG. 1, no partial withdrawal of the first residue to the second distillation column was conducted, and all the first residue was circulated to the reactor 1 via the conduit 61. Further, immediately after the initiation of the reaction, a triglyme solution containing 50% by weight of TOP was filled at the portion of the container 2 for catalyst solution, instead of the catalyst solution. Then, after one day from the initiation of the reaction, the solution was supplied at proper timing to maintain the concentration of TOP in the liquid phase in the reactor to the value shown in Table 4. After 5 days from the initiation of the reaction, the reaction results were constant. The results are shown in Table 4.

TABLE 4

| | Concentration of TOP (wt %) | Conversion of the starting material (%) | Selectivity for GBL (%) | Yield of GBL (%) |
|---|---|---|---|---|
| Example 17 | 0.04 | 100 | 96.3 | 96.3 |
| Example 18 | 0.10 | 99 | 93.9 | 93.0 |
| Example 19 | 0.15 | 98 | 87.0 | 85.3 |

EXAMPLE 20

The hydrogenation reaction was conducted in the same manner as in Example 17 except that in Example 17, no TOP was supplied from the container 2.

The concentration of free TOP in the reaction solution, the conversion of the starting material and the yield of GBL after one to seven days from the initiation of the reaction are shown in Table 5.

As shown in Table 5, the TOP concentration decreased to 0.005% by weight after 6 days from the initiation of the reaction, and it became substantially 0 after 7 days, and the yield of GBL decreased substantially. Further, it is evident that the yield of GBL drops substantially at a TOP concentration of about 0.01% by weight as the turning point.

TABLE 5

| Numbers of days passed | Concentration of TOP (wt %) | Conversion of the starting material (%) | Selectivity for GBL (%) | Yield of GBL (%) |
|---|---|---|---|---|
| 1 | 0.038 | 88 | 92 | 81 |
| 2 | 0.031 | 91 | 91 | 83 |
| 3 | 0.023 | 95 | 93 | 88 |
| 4 | 0.024 | 98 | 95 | 93 |
| 5 | 0.015 | 95 | 88 | 84 |
| 6 | 0.005 | 91 | 80 | 73 |
| 7 | less than 0.001 | 69 | 72 | 50 |

EXAMPLES 21 to 24

The operation was conducted in the same manner as the Example 1 except that the flow rate of hydrogen and the reaction temperature in the reactor 1 were set as shown in Table 6. The reaction results and the concentration of water in the liquid phase in the reactor after 12 hours from the initiation of the reaction are shown in Table 6.

From the results in Table 6, it is evident that the lower the concentration of water in the reaction solution, the better the reaction results.

TABLE 6

| | Flow rate of hydrogen | | Reaction temp. (°C.) | Conversion of the starting material (%) | Yield of GBL (%) | Concentration of water (%) |
|---|---|---|---|---|---|---|
| | (hr$^{-1}$) | NTP.l/hr | | | | |
| Example 21 | 640 | 128 | 205 | 96.3 | 92.5 | 0.28 |
| Example 22 | 960 | 192 | 205 | 98.2 | 95.5 | 0.16 |

TABLE 6-continued

|  | Flow rate of hydrogen | | Reaction temp. (°C.) | Conversion of the starting material (%) | Yield of GBL (%) | Concentration of water (%) |
| --- | --- | --- | --- | --- | --- | --- |
|  | (hr$^{-1}$) | NTP.l/hr |  |  |  |  |
| Example 23 | 20 | 4 | 200 | 89.4 | 80.9 | 1.60 |
| Example 24 | 300 | 60 | 200 | 91.2 | 84.0 | 1.10 |

According to the process of the present invention, it is possible to efficiently utilize the solvent and the catalyst during the preparation of a lactone by hydrolyzing a dicarboxilic acid, a dicarboxilic acid anhydride and/or a dicarboxilic acid ester in a liquid phase in the presence of a ruthenium catalyst, and it is possible to produce the desired product in good yield. Therefore, its value for industrial application is very high.

We claim:

1. A process for producing a lactone by reacting in a hydrogenation reaction zone a dicarboxylic acid, a dicarboxylic acid anhydride and/or a dicarboxylic acid ester with hydrogen in a liquid phase using a solvent in the presence of a catalyst comprising ruthenium and an organic phosphine, which process comprises the following steps (1) to (6)

(1) a first step of recovering the liquid phase from the hydrogenation reaction zone, (2) a second step of distilling the liquid phase in a first distillation column to obtain a first distillate and a first residue, (3) a third step of recycling the first residue to the hydrogenation reaction zone, (4) a fourth step of distilling a part of the first residue in a second distillation column to obtain a second distillate and a second residue, (5) a fifth step of recycling the second distillate to the hydrogenation reaction zone or the first distillation column, and (6) a sixth step of recovering a lactone from the first distillate.

2. The process according to claim 1, wherein the concentration of free organic phosphine in the liquid phase in the hydrogenation reaction zone is maintained within a range of from 0.01 to 0.1% by weight.

3. The process according to claim 1, wherein the concentration of water in the liquid phase in the hydrogenation reaction zone is maintained at a level of not higher than 1% by weight.

4. The process according to claim 1, wherein as the catalyst containing ruthenium and an organic phosphine, a catalyst comprising (1) ruthenium, (2) an organic phosphine and (3) a conjugate base of an acid having a pKa of less than 2.0, is employed.

5. The process according to claim 1, wherein the gas phase after the recovery of the liquid phase from the hydrogenation reaction zone is recycled for use as hydrogen.

6. The process according to claim 1, wherein the first distillate contains from 3 to 50% by weight of the solvent.

7. The process according to claim 1, wherein the bottom temperature of the sencond distillation column is maintained within a range of from 140 to 240° C.

8. The process according to claim 1, wherein a polyether is used as the solvent for reaction, and in the sixth step, the lactone is recovered by distilling the first distillate, whereby the bottom temperature of the distillation column is not higher than 150° C.

9. The process according to claim 8, wherein the residue after the distillation of the lactone is recycled to the hydrogenation reaction zone or the first distillation column.

* * * * *